(12) United States Patent
Olenik et al.

(10) Patent No.: US 8,324,253 B2
(45) Date of Patent: Dec. 4, 2012

(54) CRYSTALLINE MODIFICATION OF 4-(N-METHYL-Z-CHLORO-5PYRIDY METHYLAMINO)-2, 5-DIHYDROFURAN-2-ON

(75) Inventors: Britta Olenik, Bottrop (DE); Peter Jeschke, Bergisch Gladbach (DE); Robert Velten, Langenfeld (DE); Bernd Gallenkamp, Wuppertal (DE); Wolfgang Joerges, Odenthal (DE); Ronald Vermeer, Leverkusen (DE); Leonardo Pitta, Leverkusen (DE)

(73) Assignee: Bayer Cropscience AG, Monheim (DE)

( * ) Notice: Subject to any disclaimer, the term of this patent is extended or adjusted under 35 U.S.C. 154(b) by 567 days.

(21) Appl. No.: 12/441,763

(22) PCT Filed: Sep. 18, 2007

(86) PCT No.: PCT/EP2007/008102
§ 371 (c)(1),
(2), (4) Date: Apr. 15, 2009

(87) PCT Pub. No.: WO2008/040445
PCT Pub. Date: Apr. 10, 2008

(65) Prior Publication Data
US 2010/0069242 A1    Mar. 18, 2010

(30) Foreign Application Priority Data
Sep. 29, 2006  (DE) .......................... 10 2006 046 161

(51) Int. Cl.
*A01N 43/40* (2006.01)
*C07D 405/12* (2006.01)
(52) U.S. Cl. ..................................... 514/336; 546/284.4
(58) Field of Classification Search ............... 546/284.4; 514/336
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno | |
| 5,876,739 A | 3/1999 | Turnblad et al. | |
| 6,730,312 B2 | 5/2004 | Schneidersmann et al. | |
| 7,417,150 B2 | 8/2008 | Jeschke et al. | |
| 2008/0280953 A1 | 11/2008 | Gorgens et al. | |

FOREIGN PATENT DOCUMENTS

| | | |
|---|---|---|
| EP | 0 539 588 | 1/1992 |
| WO | 02/28186 A2 | 4/2002 |
| WO | 02/080675 A1 | 10/2002 |
| WO | 02085870 | 10/2002 |

OTHER PUBLICATIONS

Chemical & Engineering News, Feb. 2003, 32-35.*
Brittain ed., "Polymorphism in Pharmaceutical Solids.," NY:Marcel Dekker, Inc., 1999, 1-2, 183-226, 235-238.*
U.S. Pharmacopia #23, National Formulary #18, 1995, 1843-1844.*
Jain et al., "Polymorphism in Pharmacy", Indian Drugs, 1986, 23(6) 315-329.*
Concise Encyclopedia Chemistry, NY: Walter de Gruyter, 1993, 872-873.*
Ulicky. Comprehensive Dictionary of Physical Chemistry, NY: Prentice Hall, 1992, p. 21.*
Bernstein et al., "Concomitant Polymorphs," Angew. Chem. Int. Ed. 1999, vol. 38, pp. 3440-3461.
Haleblian et al., "Pharmaceutical Applications of Polymorphism," Journal of Pharmaceutical Science, Aug. 1969, vol. 58, No. 8, pp. 911.
International Search Report of PCT/EP2007/008102 dated Feb. 21, 2008 (1 page).

* cited by examiner

*Primary Examiner* — Patricia Morris
(74) *Attorney, Agent, or Firm* — Baker, Donelson, Bearman, Caldwell & Berkowitz P.C.

(57) ABSTRACT

The present invention relates to a defined crystalline modification of the compound of the formula (I), to processes for its preparation and to its use in agrochemical preparations.

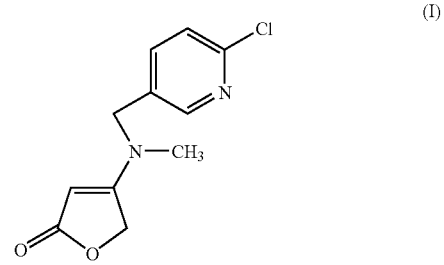

20 Claims, 6 Drawing Sheets

CRYSTALLINE MODIFICATION OF 4-(N-METHYL-Z-CHLORO-5PYRIDY METHYLAMINO)-2, 5-DIHYDROFURAN-2-ON

CROSS REFERENCE TO RELATED APPLICATIONS

This application is a §371 National Stage Application of PCT/EP2007/008102 filed Sep. 18, 2007 which claims priority to German Application 10 2006 046 161.4 filed Sep. 29, 2006.

BACKGROUND OF THE INVENTION

1. Field of the Invention

The present invention relates to a novel crystalline modification of the compound of the formula (I), to processes for its preparation and to its use in agrochemical preparations.

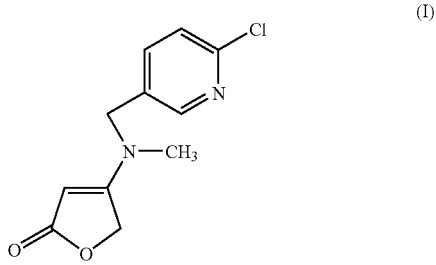

(I)

2. Description of Related Art

The compound of the formula (I) is known from EP-A 0 539 588. It can be synthesized by the processes described therein.

In the synthesis process described in the prior art, the compound of the formula (I) of the crystalline modification II (for nomenclature and characterization see further below in the description) is obtained. This crystalline modification is metastable.

It is known that for some polymorphs a certain modification is the thermodynamically stable phase over the entire temperature range up to the melting point, whereas in other substance systems there are one or more transition points in which the stability ratio is reversed. It is not possible to predict the stability ratio and in particular the existence and position of the transition points referred to above. A review of the prior art concerning these basic thermodynamic relations is given in J. Bernstein, R. J. Davey, J. O. Henck, Angew. Chem. Int. Ed., 1999, 38, 3440-3461.

The occurrence of active compounds in various crystalline modifications (polymorphism) is of major importance both for working out preparation processes and for developing formulations. Thus, the various crystalline modifications of a chemical compound differ not only in appearance (crystal habit) and hardness but also in numerous further physico-chemical properties. Differences relating to the stability, the filterability, the grindability, the solubility, the hygroscopicity, the melting point, the solids density and the flowability can have a considerable influence on the quality and the efficacy of crop treatment compositions. It has not been possible to date to predict the occurrence and the number of crystalline modifications, including their physicochemical properties. Especially the thermodynamic stability and also the different behaviour after administration in living organisms cannot be determined in advance.

Metastable crystal modifications, such as the crystalline modification II of the compound of the formula (I), generally have disadvantages compared to a thermodynamically stable form with respect to the preparation process, and also with respect to storage and the transport of the active compounds and formulations. It is known from J. Halebian, W. McCrone, J. Pharm. Sci. 58 (1969) 911, that, when a thermodynamically metastable form is used, there may be complete or partial conversion into another polymorphic form during preparation or storage. As an associated phenomenon, unwanted crystal growth (recrystallization), changes in bioavailability, agglomeration, etc., are observed. The conversion may take place over a relatively long period of time or spontaneously and cannot be predicted. Whether, when and in what amount another crystal modification is formed is essentially a matter of chance. This behaviour of metastable crystal modifications may have a large influence on development, transport and in particular on storage stability.

SUMMARY OF THE INVENTION

Furthermore, it is known that metastable crystal modifications such as the crystalline modification II of the compound of the formula (I) may, during the preparation of formulations, in particular those formulations in which the active compound is present in the solid form, or in cases where the active compound is, during preparation of the formulations, present for a certain length of time in solid form, result in negative properties of the formulation. Indeed, it cannot be excluded that it is impossible to prepare formulations when metastable crystal modifications are used. When preparing formulations in which the active compound is used in solid form, it is generally necessary to comminute the active compound. This process is mechanical, and therefore causes a temperature increase. When the temperature is increased, a thermodynamically metastable form of the active compound will tend to convert into the stable modification, which may result in seizure during grinding. Seizure during grinding is to be understood as meaning that the active compound or the suspension of active compound and the grinding medium solidify in the grinding apparatus, up to complete hardening. The risk of a seizure during grinding is influenced by the unpredictable conversion rate of the metastable modification. Even if the formulations can be prepared using an active compound of the metastable modification, the storage of the formulations frequently entails problems, since here even a very low conversion rate of the metastable modification may have a negative effect on the storage properties. Exemplary negative properties which may be caused by such a conversion during storage are crystal growth, particle agglomeration, sedimentation or solidification of the product. Accordingly, it is an object of the invention to provide a novel crystalline modification of the compound of the formula (I) which, owing to its physicochemical properties, can be handled well in formulations. A further object of the present invention is the preparation of a novel crystalline modification of the compound of the formula (I) which is particularly suitable for preparing formulations which require grinding processes to be employed. By way of example and by way of preference—but not by way of limitation—the following formulations may be mentioned: formulations in which the active compound is present in solid (dry) form, such as, for example: granules, encapsulated granules, tablets, water-dispersible granules, water-dispersible tablets, water-dispersible powders or water-dispersible powders for seed treatment, dust formulations; formulations in which the active compound is present in dispersed form, such as, for example: suspension concentrates, oil-based suspension concentrates, suspoemulsions, or suspension concentrates for seed treatment.

According to the invention, this object is achieved by a novel crystalline modification of the compound of the formula (I) which is referred to hereinbelow as crystalline modification I (stable modification).

Accordingly, the invention provides the crystalline modification I, which is characterized in that it has an x-ray powder diffractogram, when using Cu Kα radiation, with the following reflection planes (2 theta, >20% relative intensity):

| 2 Theta/° |
|---|
| 16.80 |
| 19.58 |
| 21.11 |
| 21.32 |
| 23.23 |
| 28.00 |

According to a preferred embodiment, the crystalline modification I is characterized in that it has an x-ray powder diffractogram, when using Cu Kα radiation, with the following reflection planes (2 theta, >20% relative intensity):

| 2 Theta/° |
|---|
| 16.80 |
| 19.58 |
| 21.11 |
| 21.32 |
| 22.92 |
| 23.23 |
| 23.97 |
| 28.00 |

DETAILED DESCRIPTION OF A PREFERRED EMBODIMENT

According to a further preferred embodiment, the crystalline modification I is characterized in that it has an x-ray powder diffractogram, when using Cu Kα radiation, with the following reflection planes (2 theta, >20% relative intensity):

| 2 Theta/° |
|---|
| 8.07 |
| 15.16 |
| 16.80 |
| 19.58 |
| 20.03 |
| 21.11 |
| 21.32 |
| 22.92 |
| 23.23 |

| 2 Theta/° |
|---|
| 23.97 |
| 24.46 |
| 24.54 |
| 27.26 |
| 27.60 |
| 28.00 |

According to a particularly preferred embodiment of the present invention, the x-ray powder diffractogram of the crystalline modification I has the reflection planes given in Table 1. According to a further very particularly preferred embodiment of the present invention, the x-ray powder diffractogram of the crystalline modification I has the signals shown in FIG. 1. Accordingly, the most intensive signals (2 theta) of the x-ray powder diffractogram of the crystalline modification I are at 16.80°, 19.58°, 21.11°, 21.32°, 22.92°, 23.23°, 23.97° and 28.00° (in each case ±0.2°).

All x-ray powder diffractometry data were obtained using the following acquisition parameters:

| | |
|---|---|
| Diffractometer: | Transmission |
| Monochromator: | Curved Germanium (111) |
| Wavelength: | 1.540598 Cu |
| Detector: | Linear PSD |
| Scan mode: | Transmission/Moving PSD/Fixed omega |
| Scan Type: | 2 Theta:Omega |
| 2 theta stated: | ±0.2° |

TABLE 1

| 2 Theta/° | Relative intensity[1] |
|---|---|
| 8.07 | 14 |
| 15.16 | 13 |
| 15.51 | 11 |
| 16.25 | 9 |
| 16.80 | 100 |
| 18.02 | 12 |
| 19.58 | 30 |
| 20.03 | 18 |
| 20.67 | 8 |
| 21.11 | 26 |
| 21.32 | 21 |
| 21.69 | 9 |
| 21.77 | 9 |
| 22.19 | 9 |
| 22.92 | 20 |
| 23.23 | 48 |
| 23.97 | 20 |
| 24.26 | 11 |
| 24.46 | 17 |
| 24.54 | 14 |
| 24.76 | 8 |
| 25.31 | 8 |
| 25.88 | 6 |
| 26.14 | 7 |
| 26.87 | 12 |
| 27.26 | 13 |
| 27.60 | 18 |
| 28.00 | 45 |
| 28.41 | 11 |
| 28.96 | 6 |
| 29.09 | 6 |
| 29.80 | 9 |
| 30.65 | 7 |
| 31.00 | 7 |
| 31.29 | 10 |
| 31.77 | 6 |
| 32.86 | 6 |
| 33.91 | 5 |
| 34.78 | 10 |

TABLE 1-continued

| 2 Theta/° | Relative intensity[1] |
|---|---|
| 35.47 | 6 |
| 35.78 | 4 |
| 36.57 | 10 |
| 36.86 | 3 |
| 37.16 | 7 |

[1]Intensity relative to the most intensive signal of the spectrum which is arbitrarily defined as 100.

The known crystalline modification II of the compound of the formula (I) is characterized in that it has an x-ray powder diffractogram with the reflection planes (2 theta) stated in Table 2 below. The x-ray powder diffractogram of the crystalline modification II is also shown in FIG. 2.

TABLE 2

| 2 Theta/° | Relative intensity[1] |
|---|---|
| 12.82 | 14 |
| 13.17 | 12 |
| 14.02 | 52 |
| 15.23 | 9 |
| 15.75 | 7 |
| 16.81 | 19 |
| 17.19 | 38 |
| 18.90 | 42 |
| 19.66 | 31 |
| 19.81 | 33 |
| 20.01 | 8 |
| 20.63 | 81 |
| 21.19 | 11 |
| 21.34 | 17 |
| 22.01 | 100 |
| 22.55 | 41 |
| 22.71 | 40 |
| 22.93 | 8 |
| 23.22 | 11 |
| 23.79 | 18 |
| 23.92 | 24 |
| 24.54 | 11 |
| 24.83 | 12 |
| 25.16 | 17 |
| 25.81 | 8 |
| 26.18 | 5 |
| 26.44 | 4 |
| 26.84 | 6 |
| 27.01 | 5 |
| 27.33 | 7 |
| 27.59 | 6 |
| 27.97 | 16 |
| 28.26 | 62 |
| 28.52 | 36 |
| 28.79 | 24 |
| 29.31 | 18 |
| 29.53 | 18 |
| 29.67 | 9 |
| 29.79 | 7 |
| 30.62 | 10 |
| 30.82 | 16 |
| 31.30 | 4 |
| 31.53 | 5 |
| 31.78 | 5 |
| 32.23 | 6 |
| 32.83 | 6 |
| 33.33 | 4 |
| 34.10 | 4 |
| 34.57 | 13 |
| 34.78 | 13 |
| 35.21 | 7 |
| 35.40 | 6 |
| 36.31 | 6 |
| 36.49 | 4 |
| 36.79 | 9 |

TABLE 2-continued

| 2 Theta/° | Relative intensity[1] |
|---|---|
| 36.95 | 7 |
| 37.71 | 4 |

[1]Intensity relative to the most intensive signal of the spectrum which is arbitrarily defined as 100.

The crystalline modification I according to the invention of the compound of the formula (I) may furthermore be characterized by IR and Raman spectroscopy.

Accordingly, the invention furthermore provides the crystalline modification I of the compound of the formula (I), which is characterized in that it has an IR spectrum with the following bands [cm$^{-1}$]:

| [cm$^{-1}$] |
|---|
| 3122 |
| 1584 |
| 1055 |
| 933 |
| 896 |
| 800 |

According to a preferred embodiment of the present invention, the IR spectrum of the crystalline modification I of the compound of the formula (I) has the bands given in Table 3. According to a further particularly preferred embodiment of the present invention, the IR spectrum of the crystalline modification I has the signals shown in FIG. 3.

The invention furthermore provides the crystalline modification I of the compound of the formula (I), which is characterized in that it has a Raman spectrum with the following bands [cm$^{-1}$]:

| [cm$^{-1}$] |
|---|
| 3047 |
| 1719 |
| 1601 |
| 1342 |
| 1254 |
| 936 |

According to a preferred embodiment of the present invention, the Raman spectrum of the crystalline modification I of the compound of the formula (I) has the bands given in Table 3. According to a further very particularly preferred embodiment of the present invention, the Raman spectrum of the crystalline modification I has the signals shown in FIG. 5.

The known crystalline modification II of the compound of the formula (I) is characterized in that it has an IR or Raman spectrum with the bands given in Table 3 below. The IR spectrum of the crystalline modification II and the Raman spectrum of the crystalline modification II are also shown in FIG. 4 and FIG. 6, respectively.

All IR spectra were obtained using the following acquisition parameters:

| | |
|---|---|
| FT-IR spectrometer | Bruker Tensor 37 |
| Diamond ATR unit | from Specac |
| Wavelength range | 550-4000 cm$^{-1}$ |
| Resolution | 2 cm$^{-1}$ |
| Number of scans | 64 |

All Raman spectra were obtained using the following acquisition parameters:

| | |
|---|---|
| FT-Raman spectrometer | Bruker RFS/100 |
| Laser wave number | 15798.7 cm$^{-1}$ |
| Resolution | 1 cm$^{-1}$ |
| Number of scans | 128 |

TABLE 3

| I IR bands [cm$^{-1}$] | II IR bands [cm$^{-1}$] | I Raman bands [cm$^{-1}$] | II Raman bands [cm$^{-1}$] |
|---|---|---|---|
| 800 | 720 | 335 | 183 |
| 813 | 737 | 409 | 249 |
| 854 | 749 | 415 | 270 |
| 896 | 776 | 429 | 288 |
| 933 | 814 | 457 | 312 |
| 981 | 830 | 513 | 337 |
| 990 | 852 | 547 | 387 |
| 1006 | 866 | 579 | 415 |
| 1030 | 901 | 601 | 428 |
| 1055 | 918 | 635 | 462 |
| 1106 | 948 | 675 | 503 |
| 1143 | 989 | 706 | 540 |
| 1159 | 1010 | 709 | 544 |
| 1189 | 1026 | 743 | 580 |
| 1227 | 1048 | 801 | 602 |
| 1294 | 1098 | 815 | 639 |
| 1326 | 1109 | 832 | 680 |
| 1343 | 1141 | 864 | 703 |
| 1390 | 1160 | 900 | 722 |
| 1409 | 1195 | 936 | 738 |
| 1434 | 1212 | 982 | 779 |
| 1443 | 1250 | 1030 | 814 |
| 1458 | 1288 | 1056 | 830 |
| 1567 | 1326 | 1095 | 853 |
| 1584 | 1354 | 1112 | 869 |
| 1713 | 1395 | 1142 | 900 |
| 1750 | 1415 | 1168 | 919 |
| 1797 | 1450 | 1208 | 950 |
| 2906 | 1505 | 1226 | 990 |
| 2930 | 1566 | 1254 | 993 |
| 3047 | 1607 | 1293 | 1012 |
| 3122 | 1716 | 1330 | 1029 |
| | 1802 | 1342 | 1046 |
| | 2816 | 1391 | 1092 |
| | 2871 | 1410 | 1098 |
| | 1932 | 1443 | 1110 |
| | 2953 | 1466 | 1141 |
| | 3010 | 1568 | 1167 |
| | 3058 | 1585 | 1212 |
| | 3078 | 1601 | 1222 |
| | 3126 | 1679 | 1233 |
| | | 1705 | 1250 |
| | | 1719 | 1288 |
| | | 1794 | 1293 |
| | | 2678 | 1338 |
| | | 2831 | 1355 |
| | | 2869 | 1418 |
| | | 2907 | 1449 |
| | | 2930 | 1464 |
| | | 2952 | 1568 |
| | | 2961 | 1584 |
| | | 2985 | 1619 |
| | | 3047 | 1706 |
| | | 3070 | 2816 |
| | | 3122 | 2873 |
| | | | 2934 |
| | | | 2952 |
| | | | 3057 |
| | | | 3067 |
| | | | 3126 |
| | | | 3168 |

Surprisingly, it has been found that the compound of the formula (I) in the crystalline modification I is thermodynamically stable and does not convert into another crystalline modification, even during prolonged storage. Furthermore, it has been found that, compared to other crystalline modifications, the crystalline modification I is easier to comminute/grind, and that formulations prepared using this modification are stable even after storage. This allows the preparation of suspension concentrates, oil-based suspension concentrates and, for example, water-dispersible granules and also similar formulations for treating seed. In addition, compared to the crystalline modification II, the crystalline modification I has a reduced tendency to absorb atmospheric moisture. For these reasons, it is highly suitable for preparing solid formulations. By virtue of its stability, it bestows onto these formulations the desired long-lasting storage stability. Using the crystalline modification I, it is thus possible to prepare in a defined and targeted manner stable solid preparations of the compound of the formula (I).

By virtue of its stability, the compound of the formula (I) in the crystalline modification I is highly suitable for preparing compositions for controlling pests. Accordingly, the invention also provides compositions for controlling pests comprising the crystalline modification I of the compound of the formula (I) on its own or as a mixture with auxiliaries and carriers, and also as a mixture with other active compounds.

The invention also embraces compositions comprising the crystalline modification I and the crystalline modification II of the compound of the formula (I). Preference is given to using compositions comprising less than 20% by weight of the crystalline modification II of the compound of the formula (I), particularly preferably less than 15% by weight, very particularly preferably less than 10% by weight, especially preferably less than 5% by weight, most preferably less than 4, 3, 2 or 1% by weight, of the crystalline modification II of the compound of the formula (I) for the formulation.

Preference is also given to compositions comprising from about 80 to about 100% by weight of the crystalline modification I of the compound of the formula (I) and from about 20 to about 0% by weight of the crystalline modification II of the compound of the formula (I). Particular preference is given to compositions comprising from about 85% by weight to about 100% by weight of the crystalline modification I and from about 15% by weight to about 0% by weight of the crystalline modification II. Very particular preference is given to compositions comprising from about 90% by weight to about 100% by weight of the crystalline modification I and from about 10% by weight to about 0% by weight of the crystalline modification II. Special preference is given to compositions comprising from about 95% by weight to about 100% by weight of the crystalline modification I and from about 5% by weight to about 0% by weight of the crystalline modification II. Most preference is given to compositions comprising from about 96% by weight to about 100% by weight of the crystalline modification I and from about 4% by weight to about 0% by weight of the crystalline modification II or from about 97% by weight to about 100% by weight of the crystalline modification I and from about 3% by weight to about 0% by weight of the crystalline modification II or from about 98% by weight to about 100% by weight of the crystalline modification I and from about 2% by weight to about 0% by weight of the crystalline modification II or from 99% by weight to about 100% by weight of the crystalline modification I and from about 1% by weight to about 0% by weight of the crystalline modification II.

The invention also provides compositions for controlling pests, which compositions comprise the compound of the formula (I) in the crystalline modification I and at least one form of the compound of the formula (I) which differs from the crystalline modification I. Examples of forms of the compound of the formula (I) which differ from the crystalline modification I are the crystalline modification II and the amorphous form. Preference is given to using, for formulation, an active compound quality comprising less than 20% by weight of the form of the compound of the formula (I) which differs from the crystalline modification I of the compound of the formula (I), particularly preferably less than 10% by weight, very particularly preferably less than 5% by weight and most preferably less than 2% by weight of the form of the compound of the formula (I) which differs from the crystalline modification I of the compound of the formula (I).

Owing to its stability, the crystalline modification I of the compound of the formula (I) is quite generally suitable for use as starting material for preparing any composition comprising the compound of the formula (I) for controlling pests, even if, after formulation, the compound of the formula (I) is no longer present in the crystalline modification (I), but, for example, in dissolved form.

Accordingly, the invention furthermore provides processes for preparing compositions for controlling pests using the crystalline modification I of the compound of the formula (I) and compositions comprising the compound of the formula (I) for controlling pests, which compositions were obtained from the crystalline modification I of the compound of the formula (I). By using the crystalline modification I of the compound of the formula (I), the safety of preparations of the compound of the formula (I) is increased, and the risk of dosage errors is thus reduced.

The crystalline modification I of the compound of the formula (I) can be converted in a known manner into the customary formulations, such as suspension concentrates, oil-based suspension concentrates, colloidal concentrates, dispersible concentrates, emulsifiable concentrates (emulsion concentrates), emulsion seed dressings, suspension seed dressings, granules, microgranules, suspoemulsions, water-soluble granules, water-soluble concentrates and water-dispersible granules, using suitable auxiliaries and carriers or solvents. Here, the active compound should be present in a concentration of from about 0.5 to 90% by weight of the total mixture, i.e. in amounts sufficient to achieve the required dosage level. The formulations are prepared, for example, by extending the crystalline modification I of the compound of the formula (I) with water, solvents and/or carriers, using, if appropriate, emulsifiers and/or dispersants, and/or other auxiliaries, such as, for example, penetrants.

When preparing suspension concentrates, even those used for treating seed, in addition to the active compound and an extender (water, solvent or oil), further auxiliaries are generally added. To moisten the active compound in the continuous phase, a wetting agent is used, to stabilize the suspension in the liquid phase, dispersants are used, to emulsify the non-aqueous phase, emulsifiers are used for suspension concentrates comprising solvent or oil. If required, antifreeze agents, biocides, thickeners, colorants, spreading agents and/or agents promoting uptake are incorporated.

The crystalline modification I of the compound of the formula (I) can be obtained by the processes described below.

After addition of a suitable solvent in which the compound of the formula (I) in the crystalline modification II is present in the form of a suspension, the compound of the formula (I) in the crystalline modification II (4-{[(6-chloropyrid-3-yl) methyl](methyl)amino}furan-2(5H)-one, known from EP-A 0 539 588; metastable modification) is warmed with stirring to about 80° C. (tempered) and stirred at this temperature for about one or more hours. The sample is left in the unheated block overnight. This gives the compound of the formula (I) in the crystalline modification I (stable modification).

In an alternative process, the compound of the formula (I) in the crystalline modification II (4-{[(6-chloropyrid-3-yl) methyl](methyl)amino}furan-2(5H)-one, known from EP-A 0 539 588; metastable modification) is boiled with stirring in a suitable solvent, for example butyl acetate or toluene, and stirred at reflux temperature (90-120° C.) for another 1-12 h. Heating is then switched off, the mixture is allowed to cool with stirring and a little compound of the formula (I) in the crystalline modification I (stable modification; obtainable according to Example 1) is added at about 90-110° C. After room temperature is reached, the product is filtered off with suction and washed with a suitable solvent, for example petroleum ether, toluene, hexane, heptane or cyclohexane, and the residue is dried in a vacuum drying cabinet at 30-60° C. This gives 90-95% of the compound of the formula (I) in the crystalline modification I (stable modification) and 5-10% of the compound of the formula (I) in the crystalline modification II (metastable modification).

Specific embodiments of the processes described above for preparing the crystalline modification I of the compound of the formula (I) are described in Examples 1, 1.1 and 1.2.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna con-* sanguinea, Leptinotarsa decemlineata, Lissorhoptrus oryzophilus, Lixus spp., Lyctus spp., Meligethes aeneus, Melolontha melolontha, Migdolus spp., Monochamus spp., Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga spp., Popillia japonica, Premnotrypes spp., Psylliodes chrysocephala, Ptinus spp., Rhizobius ventralis, Rhizopertha dominica, Sitophilus spp., Sphenophorus spp., Sternechus spp., Symphyletes spp., Tenebrio molitor, Tribolium spp., Trogoderma spp., Tychius spp., Xylotrechus spp., Zabrus spp.

From the order of the Collembola, for example, Onychiurus armatus.

From the order of the Dermaptera, for example, Forficula auricularia.

From the order of the Diplopoda, for example, Blaniulus guttulatus.

From the order of the Diptera, for example, Aedes spp., Anopheles spp., Bibio hortulanus, Calliphora erythrocephala, Ceratitis capitata, Chrysomyia spp., Cochliomyia spp., Cordylobia anthropophaga, Culex spp., Cuterebra spp., Dacus oleae, Dermatobia hominis, Drosophila spp., Fannia spp., Gastrophilus spp., Hylemyia spp., Hyppobosca spp., Hypoderma spp., Liriomyza spp., Lucilia spp., Musca spp., Nezara spp., Oestrus spp., Oscinella frit, Pegomyia hyoscyami, Phorbia spp., Stomoxys spp., Tabanus spp., Tannia spp., Tipula paludosa, Wohlfahrtia spp.

From the class of the Gastropoda, for example, Anion spp., Biomphalaria spp., Bulinus spp., Deroceras spp., Galba spp., Lymnaea spp., Oncomelania spp., Succinea spp.

From the class of the helminths, for example, Ancylostoma duodenale, Ancylostoma ceylanicum, Acylostoma braziliensis, Ancylostoma spp., Ascaris lubricoides, Ascaris spp., Brugia malayi, Brugia timori, Bunostomum spp., Chabertia spp., Clonorchis spp., Cooperia spp., Dicrocoelium spp, Dictyocaulus filaria, Diphyllobothrium latum, Dracunculus medinensis, Echinococcus granulosus, Echinococcus multilocularis, Enterobius vermicularis, Faciola spp., Haemonchus spp., Heterakis spp., Hymenolepis nana, Hyostrongulus spp., Loa Loa, Nematodirus spp., Oesophagostomum spp, Opisthorchis spp., Onchocerca volvulus, Ostertagia spp., Paragonimus spp., Schistosomen spp, Strongyloides fuelleborni, Strongyloides stercoralis, Stronyloides spp., Taenia saginata, Taenia solium, Trichinella spiralis, Trichinella nativa, Trichinella britovi, Trichinella nelsoni, Trichinella pseudopsiralis, Trichostrongulus spp., Trichuris trichuria, Wuchereria bancrofti.

It is furthermore possible to control protozoa, such as Eimeria.

From the order of the Heteroptera, for example, Anasa tristis, Antestiopsis spp., Blissus spp., Calocoris spp., Campylomma livida, Cavelerius spp., Cimex spp., Creontiades dilutus, Dasynus piperis, Dichelops furcatus, Diconocoris hewetti, Dysdercus spp., Euschistus spp., Eurygaster spp., Heliopeltis spp., Horcias nobilellus, Leptocorisa spp., Leptoglossus phyllopus, Lygus spp., Macropes excavatus, Miridae, Nezara spp., Oebalus spp., Pentomidae, Piesma quadrata, Piezodorus spp., Psallus seriatus, Pseudacysta persea, Rhodnius spp., Sahlbergella singularis, Scotinophora spp., Stephanitis nashi, Tibraca spp., Triatoma spp.

From the order of the Homoptera, for example, Acyrthosipon spp., Aeneolamia spp., Agonoscena spp., Aleurodes spp., Aleurolobus barodensis, Aleurothrixus spp., Amrasca spp., Anuraphis cardui, Aonidiella spp., Aphanostigma piri, Aphis spp., Arboridia apicalis, Aspidiella spp., Aspidiotus spp., Atanus spp., Aulacorthum solani, Bemisia spp., Brachycaudus helichrysii, Brachycolus spp., Brevicoryne brassicae, Calligypona marginata, Carneocephala fulgida, Ceratovacuna lanigera, Cercopidae, Ceroplastes spp., Chaetosiphon fragaefolii, Chionaspis tegalensis, Chlorita onukii, Chromaphis juglandicola, Chrysomphalus ficus, Cicadulina mbila, Coccomytilus halli, Coccus spp., Cryptomyzus ribis, Dalbulus spp., Dialeurodes spp., Diaphorina spp., Diaspis spp., Doralis spp., Drosicha spp., Dysaphis spp., Dysmicoccus spp., Empoasca spp., Eriosoma spp., Erythroneura spp., Euscelis bilobatus, Geococcus coffeae, Homalodisca coagulata, Hyalopterus arundinis, Icerya spp., Idiocerus spp., Idioscopus spp., Laodelphax striatellus, Lecanium spp., Lepidosaphes spp., Lipaphis erysimi, Macrosiphum spp., Mahanarva fimbriolata, Melanaphis sacchari, Metcalfiella spp., Metopolophium dirhodum, Monellia costalis, Monelliopsis pecanis, Myzus spp., Nasonovia ribisnigri, Nephotettix spp., Nilaparvata lugens, Oncometopia spp., Orthezia praelonga, Parabemisia myricae, Paratrioza spp., Parlatoria spp., Pemphigus spp., Peregrinus maidis, Phenacoccus spp., Phloeomyzus passerinii, Phorodon humuli, Phylloxera spp., Pinnaspis aspidis-trae, Planococcus spp., Protopulvinaria pyriformis, Pseudaulacaspis pentagona, Pseudococcus spp., Psylla spp., Pteromalus spp., Pyrilla spp., Quadraspidiotus spp., Quesada gigas, Rastrococcus spp., Rhopalosiphum spp., Saissetia spp., Scaphoides titanus, Schizaphis graminum, Selenaspidus articulatus, Sogata spp., Sogatella furcifera, Sogatodes spp., Stictocephala festina, Tenalaphara malayensis, Tinocallis caryaefoliae, Tomaspis spp., Toxoptera spp., Trialeurodes vaporariorum, Trioza spp., Typhlocyba spp., Unaspis spp., Viteus vitifolii.

From the order of the Hymenoptera, for example, Diprion spp., Hoplocampa spp., Lasius spp., Monomorium pharaonis, Vespa spp.

From the order of the Isopoda, for example, Armadillidium vulgare, Oniscus asellus, Porcellio scaber.

From the order of the Isoptera, for example, Reticulitermes spp., Odontotermes spp.

From the order of the Lepidoptera, for example, Acronicta major, Aedia leucomelas, Agrotis spp., Alabama argillacea, Anticarsia spp., Barathra brassicae, Bucculatrix thurberiella, Bupalus piniarius, Cacoecia podana, Capua reticulana, Carpocapsa pomonella, Chematobia brumata, Chilo spp., Choristoneura fumiferana, Clysia ambiguella, Cnaphalocerus spp., Earias insulana, Ephestia kuehniella, Euproctis chrysorrhoea, Euxoa spp., Feltia spp., Galleria mellonella, Helicoverpa spp., Heliothis spp., Hofmannophila pseudospretella, Homona magnanima, Hyponomeuta padella, Laphygma spp., Lithocolletis blancardella, Lithophane antennata, Loxagrotis albicosta, Lymantria spp., Malacosoma neustria, Mamestra brassicae, Mocis repanda, Mythimna separata, Oria spp., Oulema oryzae, Panolis flammea, Pectinophora gossypiella, Phyllocnistis citrella, Pieris spp., Plutella xylostella, Prodenia spp., Pseudaletia spp., Pseudoplusia includens, Pyrausta nubilalis, Spodoptera spp., Thermesia gemmatalis, Tinea pellionella, Tineola bisselliella, Tortrix viridana, Trichoplusia spp.

From the order of the Orthoptera, for example, Acheta domesticus, Blatta orientalis, Blattella germanica, Gryllotalpa spp., Leucophaea maderae, Locusta spp., Melanoplus spp., Periplaneta americana, Schistocerca gregaria.

From the order of the Siphonaptera, for example, Ceratophyllus spp., Xenopsylla cheopis.

From the order of the Symphyla, for example, Scutigerella immaculata.

From the order of the Thysanoptera, for example, Baliothrips biformis, Enneothrips flavens, Frankliniella spp.,

*Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organism) and RLO (Rickettsia-like organism). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable installations or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

According to the invention, a carrier is a natural or synthetic, organic or inorganic substance which may be solid or liquid and with which the active compounds are mixed or bonded for better applicability, in particular for application to plants or parts of plants or seed. In general, the solid or liquid carrier is inert and should be agriculturally useful.

Suitable solid or liquid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are non-ionic and/or ionic substances, for example from the classes of the alcohol-POE- and/or -POP ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The active compound content of the use forms prepared from the formulations may vary within wide ranges. The active compound concentration of the use forms is in the range from 0.00000001 to 97% by weight of active compound, preferably in the range from 0.0000001 to 97% by weight, particularly preferably in the range from 0.000001 to 83% by weight or 0.000001 to 5% by weight and very particularly preferably in the range from 0.0001 to 1% by weight.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of plant parts or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional breeding and optimization methods or by biotechnological and genetic engineering methods or by combinations of these methods, including the transgenic plants and including the plant cultivars which can or cannot be protected by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by dipping, spraying, vaporizing, fogging, broadcasting, painting on, injection and, in the case of propagation material, in particular in the case of seed, also by applying one or more coats.

Plants which can be treated according to the invention that may be mentioned are the following: cotton, flax, grapevines, fruit, vegetables, such as *Rosaceae* sp. (for example pome fruit, such as apples and pears, but also stone fruit, such as apricots, cherries, almonds and peaches, and berry fruit, such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onions), *Papilionaceae* sp. (for example peas); major useful plants, such as *Gramineae* sp. (for example maize, lawns, cereals, such as wheat, rye, rice, barley, oats, sorghum and millet and triticale), *Asteraceae* sp. (for example sunflowers), *Brassicaceae* sp. (for example white cabbage, red cabbage, broccoli, cauliflower, brussel sprouts, pak choi, kohlrabi, small radish, and also oilseed rape, mustard, horeseradish and cress), *Fabacae* sp. (for example beans, peanuts), *Papilionaceae* sp. (for example soya beans), *Solanaceae* sp. (for example potatoes), *Chenopodiaceae* sp. (for example sugar beet, fodder beet, chard, beetroot); useful plants and ornamental plants in garden and forest; and in each case genetically modified types of these plants.

The treatment according to the invention of the plants and plant parts with the active compound combinations is carried out either directly or by treating their environment, habitat or storage space by the customary treatment methods, for example by dipping, spraying, vaporizing, misting, broadcasting, painting on and, in the case of propagation material, in particular seed, furthermore by coating with one or more layers.

The mixtures according to the invention are particularly suitable for treating of seed. Preferred combinations according to the invention are in this case the combinations mentioned above as being preferred or particularly preferred. Thus, most of the damage to crop plants which is caused by pests occurs as early as when the seed is infested during storage and after the seed is introduced into the soil, and during and immediately after germination of the plants. This phase is particularly critical since the roots and shoots of the growing plants are particularly sensitive and even minor damage can lead to the death of the whole plant. Protecting the seed and the germinating plant by the use of suitable compositions is therefore of particularly great interest.

The control of pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection compositions after sowing or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection compositions being employed.

The present invention therefore in particular also relates to a method for the protection of seed and of germinating plants from attack by pests, by treating the seed with a composition according to the invention. The invention likewise relates to the use of the compositions according to the invention for the treatment of seed for protecting the seed and the resulting plants from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plants after emergence, from pests. In this manner, the immediate treatment of the crop at the time of sowing or shortly thereafter can be dispensed with.

A further advantage is the synergistically increased insecticidal activity of the compositions according to the invention in comparison with the individual insecticidally active compound, which exceeds the expected activity of the two active compounds when applied individually. Also advantageous is the synergistically increased fungicidal activity of the compositions according to the invention in comparison with the individual fungicidally active compound, which exceeds the expected activity of the active compound when applied individually. This makes possible an optimization of the amount of active compounds employed.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and, additionally, the compositions according to the invention provide protection from damage.

The compositions according to the invention are suitable for protecting seed of any plant variety as already mentioned above which is employed in agriculture, in the greenhouse, in forests or horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European maize borer and/or the maize root worm. It is particularly preferably a heterologous gene derived from *Bacillus thuringiensis*.

Within the scope of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, that is to say without further components and without having been diluted. As a rule, it is preferable to apply the compositions to the seed in the form of a suitable formulation. Suitable formulations and methods for the treatment of seed are known to the skilled worker and are described, for example, in the following documents: U.S. Pat. No. 4,272, 417 A, U.S. Pat. No. 4,245,432 A, U.S. Pat. No. 4,808,430 A, U.S. Pat. No. 5,876,739 A, US 2003/0176428 A1, WO 2002/ 080675 A1, WO 2002/028186 A2.

The active compounds which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds with customary additives, such as, for example, customary extenders and also solvents or diluents, colorants, wetting agents, dispersants, emulsifiers, antifoams, preservatives, secondary thickeners, adhesives, gibberellins and also water.

Suitable colorants that may be present in the seed dressing formulations which can be used according to the invention include all colorants customary for such purposes. Use may be made both of pigments, of sparing solubility in water, and of colorants, which are soluble in water. Examples that may be mentioned include the colorants known under the designations Rhodamine B, C.I. Pigment Red 112, and C.I. Solvent Red 1.

Suitable wetting agents that may be present in the seed dressing formulations which can be used according to the invention include all substances which promote wetting and are customary in the formulation of active agrochemical compounds. With preference it is possible to use alkylnaphthalenesulphonates, such as diisopropyl- or diisobutylnaphthalenesulphonates.

Suitable dispersants and/or emulsifiers that may be present in the seed dressing formulations which can be used according to the invention include all nonionic, anionic, and cationic dispersants which are customary in the formulation of active agrochemical compounds. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates.

Suitable antifoams that may be present in the seed dressing formulations which can be used according to the invention include all foam-inhibiting substances which are customary in the formulation of active agrochemical compounds. With preference it is possible to use silicone defoamers and magnesium stearate.

Suitable preservatives that may be present in the seed dressing formulations which can be used according to the invention include all substances which can be used for such purposes in agrochemical compositions. By way of example, mention may be made of dichlorophen and benzyl alcohol hemiformal.

Suitable secondary thickeners that may be present in the seed dressing formulations which can be used according to the invention include all substances which can be used for such purposes in agrochemical compositions. Preferred suitability is possessed by cellulose derivatives, acrylic acid derivatives, xanthan, modified clays, and highly disperse silica.

Suitable adhesives that may be present in the seed dressing formulations which can be used according to the invention include all customary binders which can be used in seed dressings. With preference, mention may be made of polyvinylpyrrolidone, polyvinyl acetate, polyvinyl alcohol and tylose.

Preferred gibberellins which may be present in the seed dressing formulations which can be used according to the invention are the gibberellins A1, A3 (=gibberellinic acid), A4 and A7; particular preference is given to using gibberellinic acid. The gibberellins are known (cf. R. Wegler "Chemie der Pflanzenschutz- and Schadlingsbekampfungsmittel", Vol. 2, Springer Verlag, 1970, pp. 401-412).

The seed dressing formulations which can be used according to the invention may be used directly or after dilution with water beforehand to treat seed of any of a very wide variety of types including the seed of transgenic plants. In this context, synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula (I) and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., Pneumonyssus spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reductions in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used according to the invention in animal husbandry, for example for cattle, poultry, pets and the like, the active compounds or compositions can be used as suitable formulations, for example powders, emulsions, free-flowing compositions. Usually suitable formulations comprise the active compounds in a concentration in the range from 0.1 to 80% by weight, preferably in the range from 1 to 60% by weight, particularly preferably in the range from 5 to 30% by weight. The formulations can be applied directly or after 100 to 10 000-fold dilution. The active compounds or compositions can also be used as a chemical bath.

It has furthermore been found that the compounds according to the invention have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood, processed wood products and coating compositions.

The ready-to-use compositions may, if appropriate, comprise further insecticides and, if appropriate, one or more fungicides.

The compounds according to the invention can likewise be employed for protecting objects which come into contact with seawater or brackish water, such as hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyci-* phagus domesticus, Ornithodorus moubat, Rhipicephalus sanguineus, Trombicula alfreddugesi, Neutrombicula autumnalis, Dermatophagoides pteronissimus, Dermatophagoides forinae.

From the order of the Araneae, for example, Avicullariidae, Araneidae.

From the order of the Opiliones, for example, Pseudoscorpiones chelifer, Pseudoscorpiones cheiridium, Opiliones phalangium.

From the order of the Isopoda, for example, Oniscus asellus, Porcellio scaber.

From the order of the Diplopoda, for example, Blaniulus guttulatus, Polydesmus spp.

From the order of the Chilopoda, for example, Geophilus spp.

From the order of the Zygentoma, for example, Ctenolepisma spp., Lepisma saccharina, Lepismodes inquilinus.

From the order of the Blattaria, for example, Blatta orientalis, Blattella germanica, Blattella asahinai, Leucophaea maderae, Panchlora spp., Parcoblatta spp., Periplaneta australasiae, Periplaneta americana, Periplaneta brunnea, Periplaneta fuliginosa, Supella longipalpa.

From the order of the Saltatoria, for example, Acheta domesticus.

From the order of the Dermaptera, for example, Forficula auricularia.

From the order of the Isoptera, for example, Kalotermes spp., Reticulitermes spp.

From the order of the Psocoptera, for example, Lepinatus spp., Liposcelis spp.

From the order of the Coleoptera, for example, Anthrenus spp., Attagenus spp., Dermestes spp., Latheticus oryzae, Necrobia spp., Ptinus spp., Rhizopertha dominica, Sitophilus granarius, Sitophilus oryzae, Sitophilus zeamais, Stegobium paniceum.

From the order of the Diptera, for example, Aedes aegypti, Aedes albopictus, Aedes taeniorhynchus, Anopheles spp., Calliphora erythrocephala, Chrysozona pluvialis, Culex quinquefasciatus, Culex pipiens, Culex tarsalis, Drosophila spp., Fannia canicularis, Musca domestica, Phlebotomus spp., Sarcophaga carnaria, Simulium spp., Stomoxys calcitrans, Tipula paludosa.

From the order of the Lepidoptera, for example, Achroia grisella, Galleria mellonella, Plodia interpunctella, Tinea cloacella, Tinea pellionella, Tineola bisselliella.

From the order of the Siphonaptera, for example, Ctenocephalides canis, Ctenocephalides felis, Pulex irritans, Tunga penetrans, Xenopsylla cheopis.

From the order of the Hymenoptera, for example, Camponotus herculeanus, Lasius fuliginosus, Lasius niger, Lasius umbratus, Monomorium pharaonis, Paravespula spp., Tetramorium caespitum.

From the order of the Anoplura, for example, Pediculus humanus capitis, Pediculus humanus corporis, Pemphigus spp., Phylloera vastatrix, Phthirus pubis.

From the order of the Heteroptera, for example, Cimex hemipterus, Cimex lectularius, Rhodinus prolixus, Triatoma infestans.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

Figure 1:
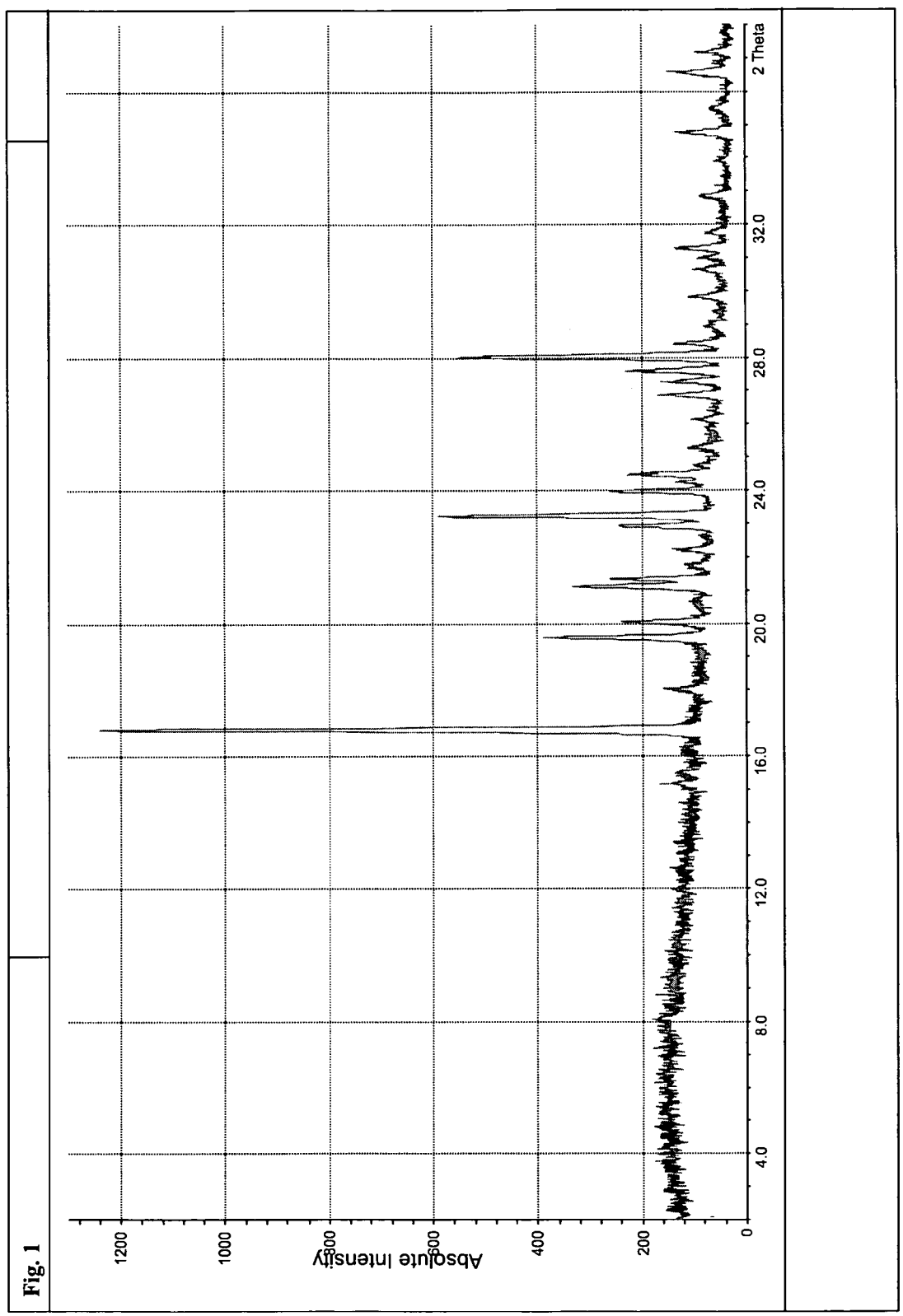
FIG. 1: X-ray powder diffractogram of the crystalline modification I of the compound of the formula (I)
Figure 2:
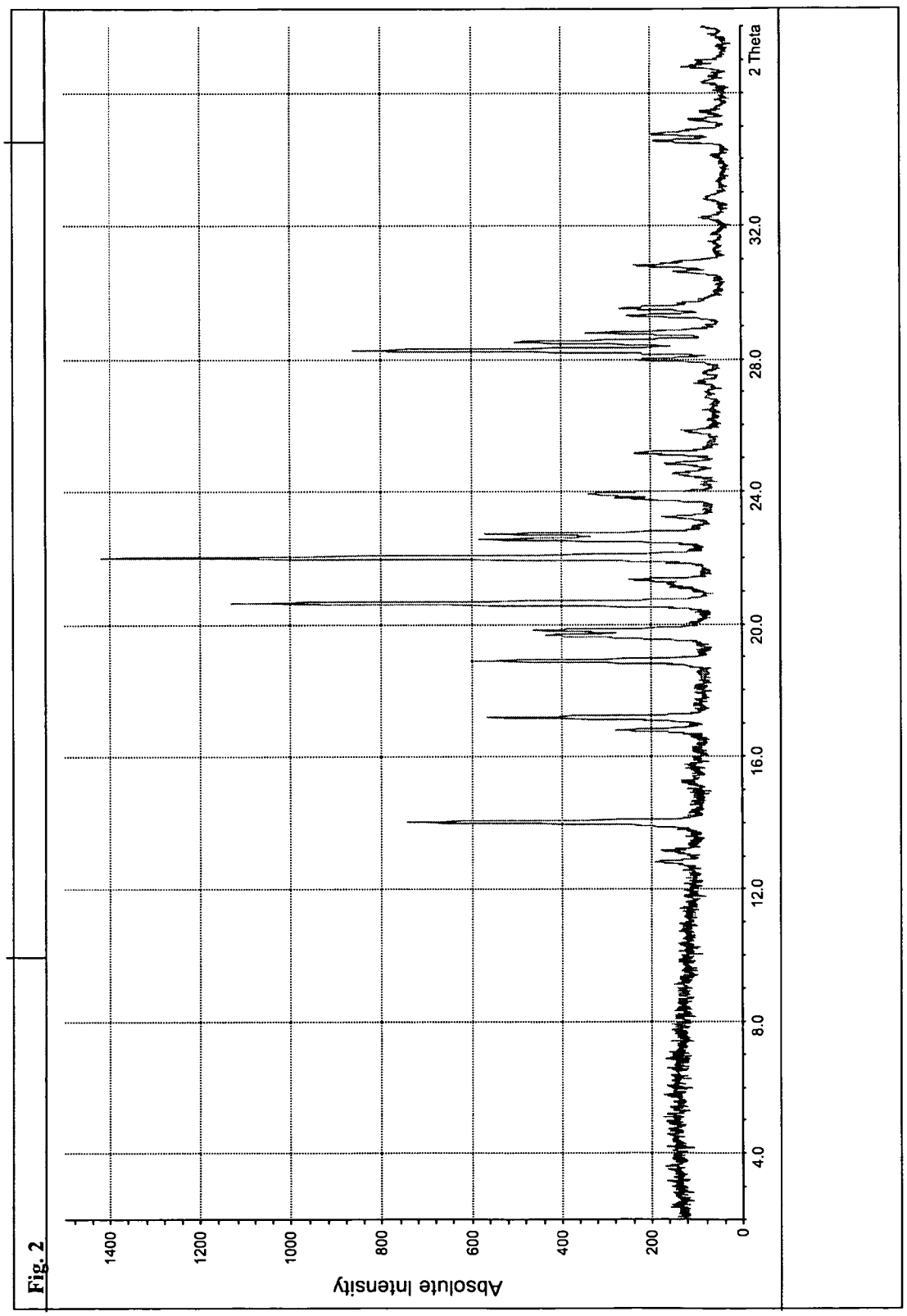
FIG. 2: X-ray powder diffractogram of the crystalline modification II of the compound of the formula (I)
Figure 3:
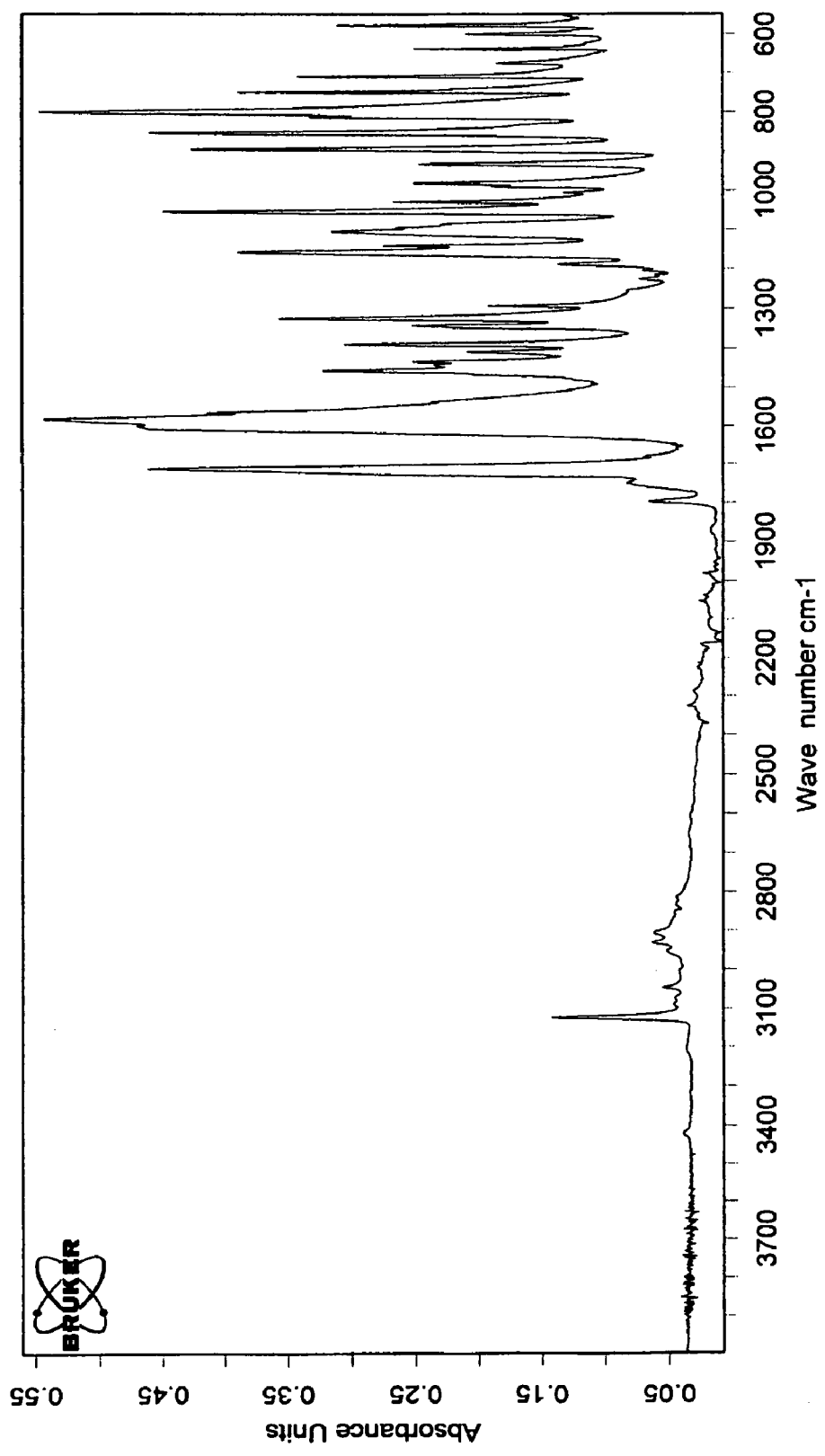
FIG. 3: IR spectrum of the crystalline modification I of the compound of the formula (I)
Figure 4:
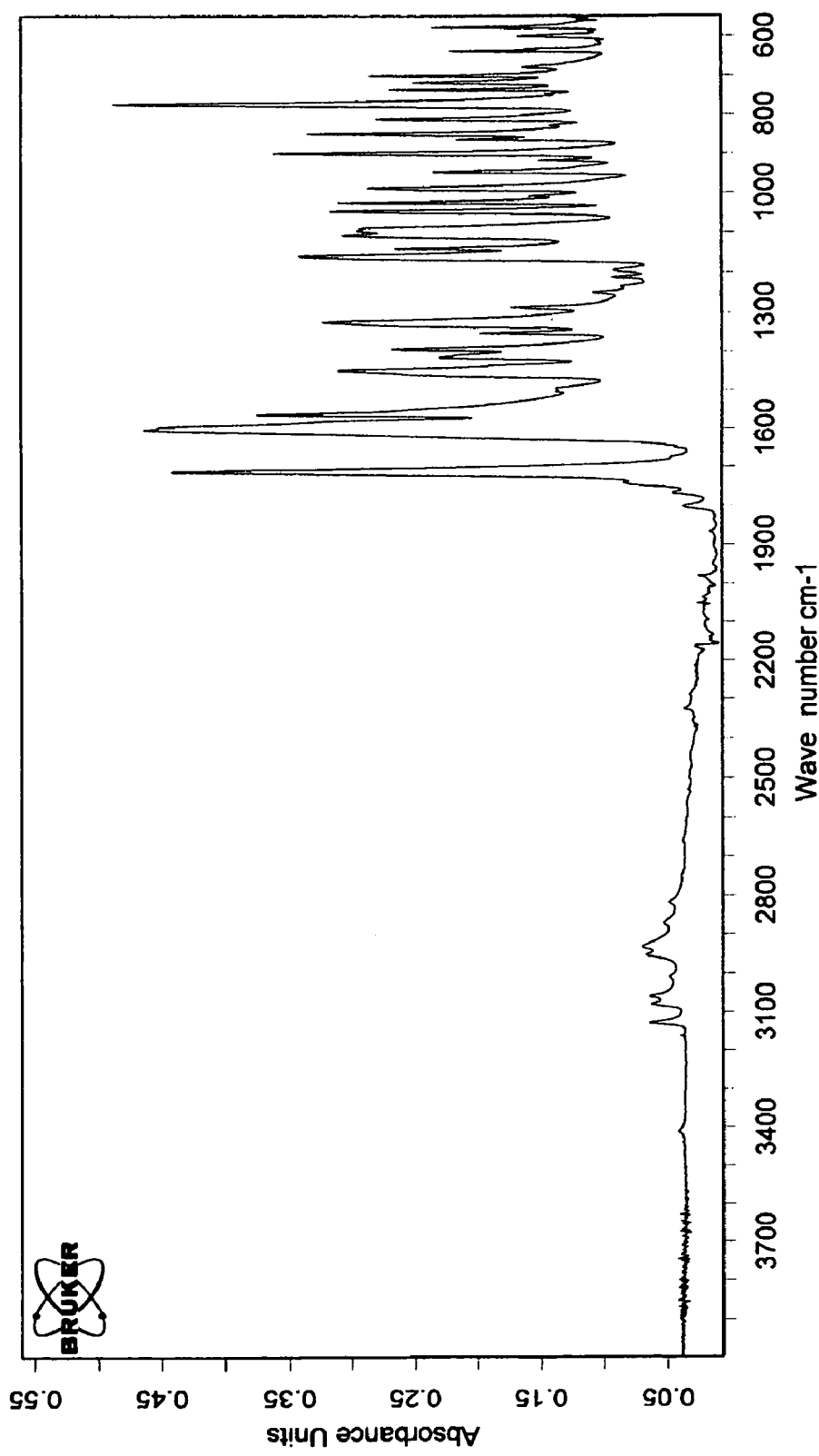
FIG. 4: IR spectrum of the crystalline modification II of the compound of the formula (I)
Figure 5:
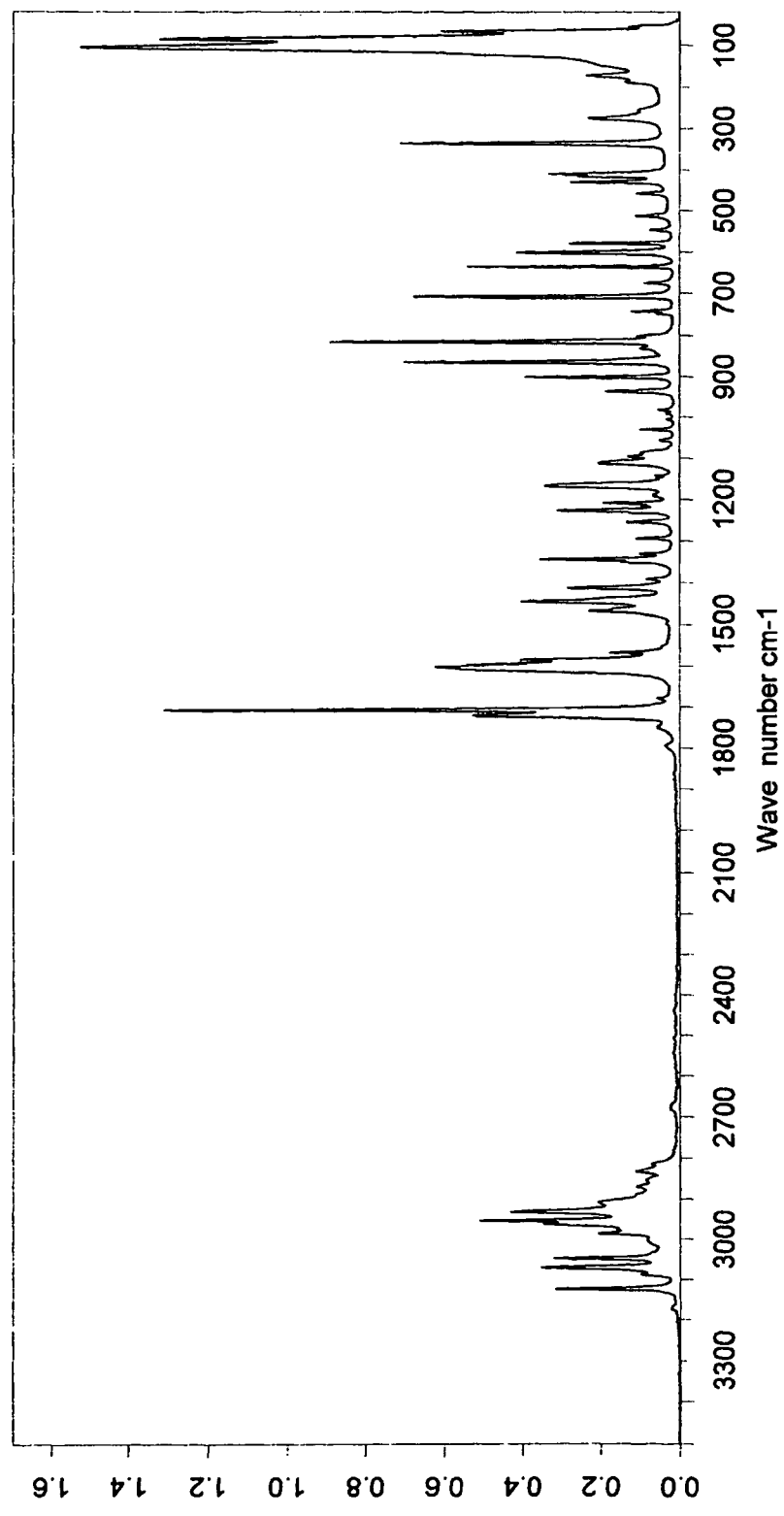
FIG. 5: Raman spectrum of the crystalline modification I of the compound of the formula (I)
Figure 6:
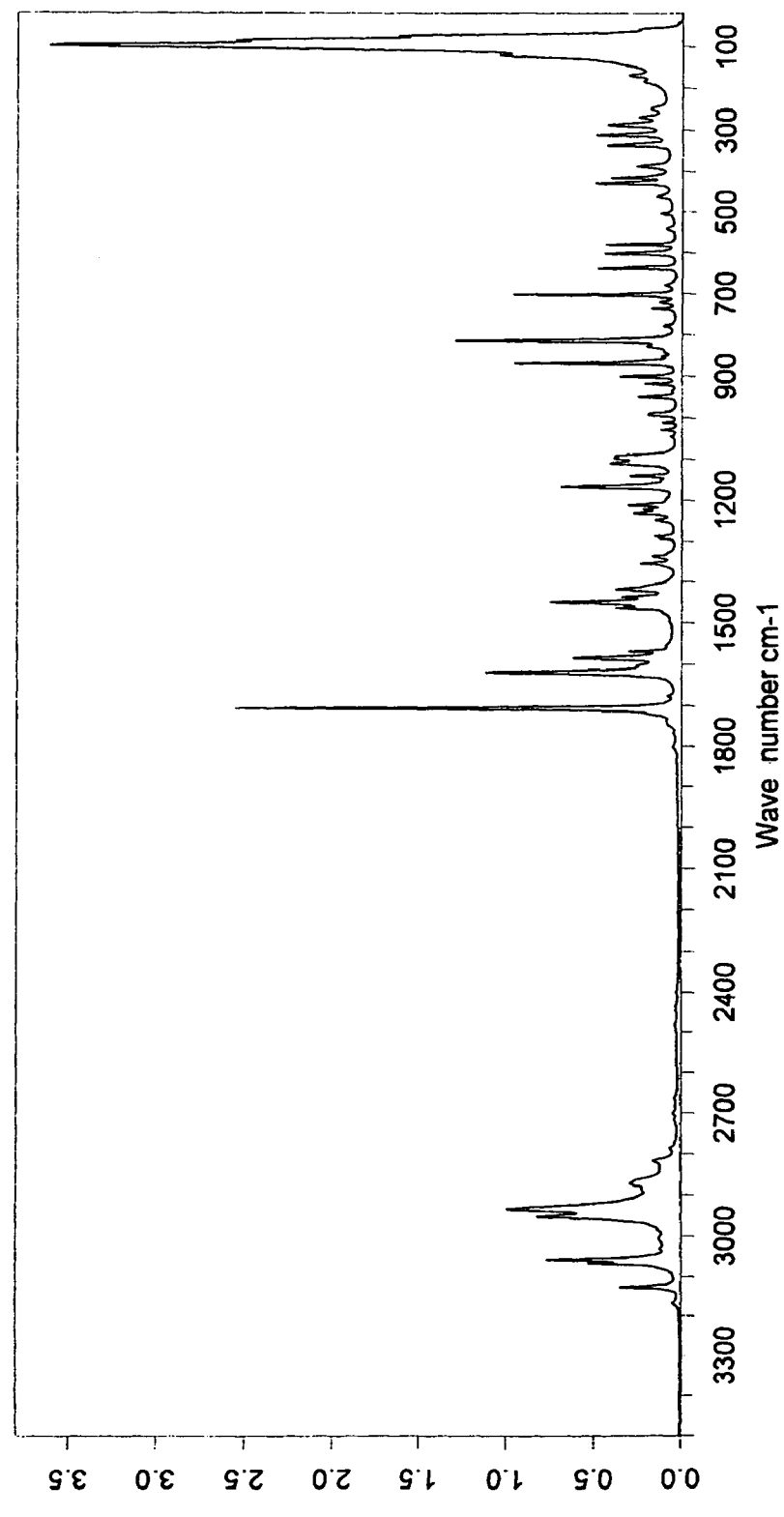
FIG. 6: Raman spectrum of the crystalline modification II of the compound of the formula (I)

The examples below illustrate the invention without limiting it. The solvent systems employed in the examples below are particularly preferred.

EXAMPLE 1

Preparation of the Compound of the Formula (I) in the Crystalline Modification I After addition of 4 drops of dist. water, 120 mg of the compound of the formula (I) in the crystalline modification II (4-{[(6-chloropyrid-3-yl)methyl](methyl)amino}furan-2 (5H)-one, known from EP-A 0 539 588; metastable modification) are warmed with stirring to 80° C. and stirred at this temperature for about another 3 hours. The sample is left in the unheated block overnight. This gives the compound of the formula (I) in the crystalline modification I (stable modification).

EXAMPLE 1.1

Preparation of the Compound of the Formula (I) in the Crystalline Modification I in the Presence of a Diluent With stirring, 200 g of the compound of the formula (I) in the crystalline modificiation II (4-{[(6-chloropyrid-3-yl)methyl](methyl)amino}furan-2(5H)-one, known from EP-A 0 539 588; metastable modification) were boiled with 400 ml of butyl acetate and stirred at reflux temperature (120° C.) for another hour. Heating is then switched off, the mixture is allowed to cool with stirring, and at about 100° C. a little compound of the formula (I) in the crystalline modification I (stable modification; cf. Example 1) is added.

Once room temperature is reached, the mixture is filtered off with suction, the product is washed with 250 ml of petroleum ether and the residue is dried in a vacuum drying cabinet at 45° C.

This gives 189.1 g of a solid (HPLC 98.0%) which comprises 90-95% of the compound of the formula (I) in the crystalline modification I (stable modification) and 5-10% of the compound of the formula (I) in the crystalline modification II (metastable modification).

EXAMPLE 1.2

Preparation of the Compound of the Formula (I) in the Crystalline Modification I without Diluent In an oil bath, 4.5 g of the compound of the formula (I) in the crystalline modification II (4-{[(6-chloropyrid-3-yl)methyl](methyl)amino}furan-2(5H)-one, known from EP-A 0 539 588; metastable modification) are melted at 125° C. and cooled to 105° C., a seed crystal (compound of the formula (I) in the crystalline modification I; stable modification; cf. Example 1) is added and the melt is cooled to room temperature.

This gives 4.4 g of crystals; 85-90% of the compound of the formula (I) in the crystalline modification I (stable modification), 10-15% of the compound of the formula (I) in the crystalline modification II (metastable modification).

EXAMPLE 2

Preparation of a Suspension Concentrate

To prepare a suspension concentrate, initially all liquid components are mixed. In the next step, the solids are added and the mixture is stirred until a homogeneous suspension is formed. The homogeneous suspension is then subjected initially to coarse grinding and then to fine grinding, such that a suspension is obtained in which 90% of the solids particles have a particle size of less than 10 μm. During grinding, it is important that the pressure in the mill remains constant and the temperature does not exceed 40° C. to prevent seizure during grinding. At room temperature, Kelzan® S and water are then added with stirring. This gives a homogeneous suspension concentrate.

EXAMPLE 2.1

Preparation of a Suspension Concentrate of the Crystalline Modification I

To prepare a suspension concentrate of the crystalline modification I of the compound of the formula (I),
43.3 g of crystalline modification I (>95%) of the formula (I)
8.0 g of Soprophor TS 29
2.0 g of Atlox 4913
20 g of glycerol
0.8 g of Kelzan S
0.16 g of Preventol D7
0.240 g of Proxel GXL
0.2 g of Silicon Antischaumemulsion SRE and
145.3 g of water
are processed as described.

EXAMPLE 2.2

Preparation of a Suspension Concentrate of the Crystalline Modification II/Comparative Formulation To prepare a suspension concentrate of the crystalline modification II of the compound of the formula (I),
43.6 g of crystalline modification II (>95%) of the formula (I)
8.0 g of Soprophor TS 29
2.0 g of Atlox 4913
20 g of glycerol
0.8 g of Kelzan S
0.16 g of Preventol D7
0.240 g of Proxel GXL
0.2 g of Silicon Antischaumemulsion SRE and
145.0 g of water
are processed as described.

EXAMPLE 2.3

Preparation of an Oil-Based Suspension Concentrate (OD) of the Crystalline Modification I To prepare an oil-based suspension concentrate (OD) of the crystalline modification I of the compound of the formula (I) in a concentration of 100 g of active compound/l (OD 100 formulation),
298 g of crystalline modification I (>85%) of the formula (I)
295 g of Arlaton T(V)
132.8 g of Atlox 4894
14.7 g of Morwet D 425
1.5 g of Silfoam SC 1132
5.9 g of anhydrous citric acid
5.9 g of Vulkanox BHT
are added with stirring at room temperature to a mixture of
590 g of the compound of the formula (II)

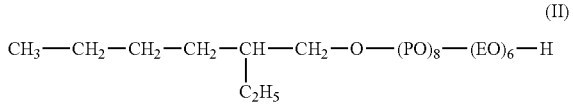

in which

EO represents —CH$_2$—CH$_2$—O—,

PO represents —CH$_2$—CH(CH$_3$)—O— and the numbers 8 and 6 are average values, and
1606 g of sunflower oil.

After the addition has ended, the mixture is stirred at room temperature for another 10 minutes. The resulting homogeneous suspension is subjected initially to coarse grinding and then to fine grinding such that a suspension is obtained in which 90% of the solids particles have a particle size of less than 6 μm.

The components, defined by their trade names, of the compositions according to the invention can be obtained from the following sources:

| Trade name | Source |
|---|---|
| Arlaton T(V) | Uniqema |
| Atlox 4913 | Uniqema |
| Atlox 4894 | Uniqema |
| Kelzan S | CP Kelco |
| Morwet D 425 | Akzo Nobel |
| Preventol D7 | Bayer AG |
| Proxel GXL | Bayer AG |
| Silfoam SC 1132 | Wacker Silicones |
| Silicon Antischaumemulsion SRE | Wacker Silicones |
| Soprophor TS 29 | Rhodia |
| Vulkanox BHT | Bayer AG |

EXAMPLE 3

Preparation Properties

The preparation of the formulation of Example 2.1 on a Dispermat® SL from Getzmann GmbH was carried out using standard settings; glass beads of a size of 0.75 to 1.0 mm, degree of filling 80%, 4000 rotations per second, throughput 0.3 l/hour, maximum temperature in the mill 36° C. at a pressure of <0.01 bar.

When the formulation of Example 2.2 was prepared on a Dispermat® SL, the throughput had to be reduced to 0.1 l/hour to prevent seizure during grinding. Owing to a strong temperature increase and increasing pressure, it would not have been possible to prepare the formulation of Example 2.2 without reducing throughput.

EXAMPLE 4

Storage Properties

The formulations of Examples 2.1 and 2.2 were stored at 54° C. for 8 weeks. After storage, the sample was brought to room temperature, and the properties of the stored formulations were compared to those of samples freshly prepared according to Example 2.

The formulation of Example 2.1 showed a slight phase separation but was readily redispersible. The formulation properties of the formulation were unchanged after storage.

The comparative formulation of Example 2.2 showed a slight phase separation, which was redispersible after intense shaking. Also observed was crystal growth and strong agglomeration of the individual particles. Within an hour, the 1% strength aqueous spray liquor prepared from this formulation formed a sediment, and it was therefore difficult to apply.

BIOLOGICAL EXAMPLE

Action of the crystalline modification I of the compound of the formula (I) against plant-damaging insects/outdoor trial rice, Philippines
*Nilaparvata lugens* Test (Foliar Application)

To produce a suitable preparation of active compound, the oil-based suspension concentrate prepared according to Example 2.3 (OD 100 formulation) was diluted with water to the desired concentration. After the desired period of time, the kill in % was determined 100% means that all leafhoppers have been killed; 0% means that none of the leafhoppers have been killed.

In this test, the compound of the formula (I) in the crystalline modification I showed good activity:

| Active compound concentration in g/ha: | 200 |
| Kill rate in % after 14 days: | 100 |

The invention claimed is:

1. Crystalline modification I of the compound of formula (I)

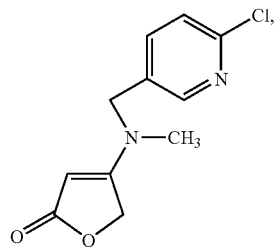

wherein an x-ray powder diffractogram thereof, when using Cu Kα radiation, has the following reflection planes

| 2 Theta/° |
| --- |
| 16.80 |
| 19.58 |
| 21.11 |
| 21.32 |
| 23.23 |
| 28.00. |

2. Crystalline modification I of a compound of formula I

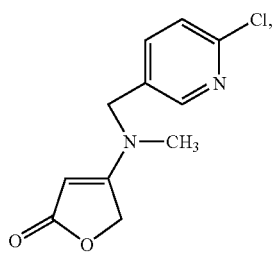

wherein an x-ray powder diffractogram thereof, when using Cu Kα radiation, has the following reflection planes

| 2 Theta/° |
| --- |
| 16.80 |
| 19.58 |
| 21.11 |
| 21.32 |
| 22.92 |
| 23.23 |
| 23.97 |
| 28.00. |

3. A composition comprising the crystalline modification I of formula (I) according to claim 1 and at least one auxiliary.

4. A composition comprising the crystalline modification I of the compound of formula (I) according to claim 1, the crystalline modification II of the compound of formula (I) and at least one suitable auxiliary, wherein the composition comprises not more than 20% by weight of the crystalline modification II of the compound of formula (I).

5. A method for controlling pests comprising using the compound of formula (I) of the crystalline modification I according to claim 1.

6. A method for controlling pests of plants comprising using the compound of formula (I) of the crystalline modification I according to claim 1.

7. A method for controlling animal parasites comprising using the compound of formula (I) of the crystalline modification I according to claim 1.

8. A method for controlling insects which destroy industrial materials comprising using the compound of formula (I) of the crystalline modification I according to claim 1.

9. A method for treating seed comprising using the compound of formula (I) of the crystalline modification I according to claim 1.

10. A method for controlling unwanted insects, comprising applying the compound of formula (I) of the crystalline modification I according to claim 1 to the insects and/or their habitat and/or seed.

11. A composition comprising the crystalline modification I of the compound of formula (I) according to claim 2 and at least one auxiliary.

12. A composition comprising the crystalline modification I of the compound of formula (I) according to claim 2, the crystalline modification II of the compound of formula (I) and at least one suitable auxiliary, wherein the composition comprises not more than 20% by weight of the crystalline modification II of the compound of formula (I).

13. A method for controlling pests comprising using the compound of formula (I) of the crystalline modification I according to claim 2.

14. A method for controlling pests of plants comprising using the compound of formula (I) of the crystalline modification I according to claim 2.

15. A method for controlling animal parasites comprising using the compound of formula (I) of the crystalline modification I according to claim 2.

16. A method for controlling insects which destroy industrial materials comprising using the compound of formula (I) of the crystalline modification I according to claim 2.

17. A method for treating seed comprising using the compound of formula (I) of the crystalline modification I according to claim 2.

18. A method for controlling unwanted insects, characterized in that a comprising applying the compound of formula (I) of the crystalline modification I according to claim 2 to the insects and/or their habitat and/or seed.

19. Seed treated by a method according to claim 17.

20. Seed treated by a method according to claim 9.

* * * * *